United States Patent
Armbruster et al.

(10) Patent No.: US 6,537,534 B1
(45) Date of Patent: Mar. 25, 2003

(54) WHOLE BODY SKIN ENHANCEMENT WATERLESS SHAVING SYSTEM AND GEL CREAMS USED THEREIN

(76) Inventors: Joseph M. Armbruster, 2700 NE. 47 St., Lighthouse Point, FL (US) 33064; Sue B. Armbruster, 2700 NE. 47 St., Lighthouse Point, FL (US) 33064

( * ) Notice: Subject to any disclaimer, the term of this patent is extended or adjusted under 35 U.S.C. 154(b) by 1598 days.

(21) Appl. No.: 08/550,002

(22) Filed: Oct. 30, 1995

Related U.S. Application Data

(63) Continuation-in-part of application No. 08/317,813, filed on Oct. 4, 1994, now abandoned.

(51) Int. Cl.$^7$ ................................................. A61K 7/15
(52) U.S. Cl. .......................................................... 424/73
(58) Field of Search ............................................ 424/73

(56) References Cited

U.S. PATENT DOCUMENTS 5,387,412 A * 2/1995 Moore ......................... 424/73

* cited by examiner

Primary Examiner—James M. Spear
(74) Attorney, Agent, or Firm—Jacobson Holman PLLC

(57) ABSTRACT

A waterless shaving system including a method of shavings consisting of the steps of applying a shaving product in the form of a thin transparent film of lubricant gel cream to a dry, unwetted skin surface area to be shaved thus leaving the hair in an erect and substantially rigid condition as compared to hair that has been wetted and soaked which results in the hair being hydrated and becoming limp and easily flexed or bent away from a razor blade when the blade comes into contact with the hair shaft in order to cut the erect hair shafts in a straight, transverse manner closely adjacent the skin surface area being shaved. The residual shaving product is rubbed into the skin area without washing off or rinsing off the skin area with water.

14 Claims, No Drawings

WHOLE BODY SKIN ENHANCEMENT WATERLESS SHAVING SYSTEM AND GEL CREAMS USED THEREIN

CROSS REFERENCE TO RELATED APPLICATION

This application is a continuation-in-part of our copending application U.S. Ser. No. 08/317,813 for RESILIENT WATERLESS SHAVING SYSTEM AND GEL CREAMS USED THEREIN filed Oct. 4, 1994 now abondoned.

BACKGROUND OF THE INVENTION

1. Field of the Invention

The present invention generally relates to a waterless shaving system in which a shaving product in the form of a gel cream and a blade razor are utilized. In this system, the skin area to be shaved is not washed and saturated with water before shaving and the skin area is not washed off to remove residual shaving product after shaving. Rather, a gel cream is applied to dry, unwetted skin to permit closer shaving enabled by the hair remaining erect which enables the hair to be cut generally perpendicular to the hair shaft axis and closer to the skin surface as compared to an inclined cut made in a "laid over", wet, limp hair. After shaving with a resilient razor and blade assembly with exhaust ports, the residual shaving product is rubbed into the skin surface.

2. Description of the Prior Art

Conventional shaving techniques currently practiced include the use of shaving creams, soaps, gels and other topical applications combined with conventional blade shaving. In using presently known shaving systems, the skin area to be shaved is usually washed with soap and saturated with water before the shaving material is applied thus requiring a source of water to be available for conventional blade shaving. The shaving materials or products generate an excessive amount of lather or foam regardless of whether gel, cream or soap is used. The excessive lather has no ability to add to shaving comfort and thus does not enhance the shaving function. Also, the thick, white foam or lather that is produced conceals pimples, moles and other skin blemishes when shaving which frequently results in the conventional razor and blade nicking or cutting the skin surface which results in larger blemishes, sores and potential infection.

Women shave in a wet, slippery hazardous tub or shower environment which increases the possibility of slipping and falling especially when standing on one leg while shaving the other leg. Also, the moisture in the tub or shower environment makes it virtually impossible to wear eyeglasses which further promotes the possibility of the skin surface being nicked, cut or areas missed during the shaving operation.

In addition, existing shaving products lack effective lubrication and frequently cause the razor blade to tend to hang which can result in cuts and nicks and when the razor and blade are repeatedly moved over a skin area which is necessary in some instances, razor burn or abrasion is sometimes caused. During shaving, the razor and blade are frequently rinsed to clean the razor and blade. After shaving, the residual shaving products must be washed off the skin to prevent skin irritation and possible skin damage. Since present shaving products are essentially soap, the skin is left dry and usually abraded thereby necessitating the use of some type of after shave lotion or emollient, frequently with an antiseptic, in an effort to cure the damage, cool or relieve the pain and heal the abraded or cut skin. A person who has shaved using conventional procedures and desires skin enhancement or protection which is the case with most men and almost all women, it is necessary to apply a moisturizer or other skin enhancement material. The present invention eliminates this necessity as the residual gel cream on the skin surface after shaving includes moisturizers as well as other skin enhancement material.

Numerous prior patents exist regarding conventional razor blades, razors and shaving products. U.S. Pat. No. 5,204,093 discloses a shaving cream composition for treatment of certain skin conditions but still teaches the concept of washing the area to be shaved prior to use of the shaving cream and after completing the shaving procedure. Such devices and products are not relevant to the present invention.

SUMMARY OF THE INVENTION

An object of the present invention is to provide a shaving system and gel creams used in the system which are applied to dry, unwetted skin which enables the hair to remain dry and erect to enable closer shaving as compared to wet, limp, "laid over" hair in which the blade will make a diagonal cut through the hair shaft since the wet hair shaft will tend to bend away from the razor blade as the sharp edge of the blade approaches and contacts the hair shaft.

Another object of the invention is to provide a shaving system and gel creams which are clear/translucent in order to enable observation of pimples, moles, skin blemishes or the like when shaving thereby avoiding cutting or nicking of these areas of the skin.

A further object of the invention is to provide a shaving system and gel creams in accordance with the preceding objects in which the gel creams include lubricating properties to prevent "dry" skin areas that may cause the razor to "grab" the skin surface which may result in nicks, cuts and razor rash or burn to provide the closest possible shave with a level of comfort that avoids scraping, cutting, nicking and razor rash requiring no water at all for shaving to permit blade shaving anywhere without the limitations of needing water for blade shaving or electricity for electric razor shaving.

Still another object of the invention is to provide a shaving system and gel creams in which the gel creams have a consistency or viscosity to avoid clogging the razor blade cartridge or razor head and blade assembly with the gel cream being thick enough to trap and hold the cut hair for discharge through large exhaust ports behind and under the blade and in communication with the sharpened edge area of the blade. If the blade is to be reused, it may be desirable to rinse the blade which need not be done immediately after shaving thereby providing a waterless shave.

A still further object of the invention is to provide a shaving system and gel cream in which the light residual gel cream remaining on the skin area after shaving is not washed off but is rubbed briskly into any area that has been shaved and including nonshaved areas such as the forehead, nose, neck, elbows, knees, feet and the like for total skin moisturization and enhancement.

Still another significant feature of the present invention is to provide a shaving system and gel creams that enable women to shave skin areas in any desired location thereby eliminating the hazards of a woman shaving in a wet, slippery and possibly dark and hazardous tub or shower which has been known to contribute to numerous slips and falls which can cause physical injury and frequent nicks and cuts from the awkward shaving procedure. Women who have vision, weight or agility problems including the elderly and those that are physically-challenged are at substantial risk when wet shaving with conventional shaving products in a bathtub or shower. This invention enables women to shave in a well lighted, dry, comfortable and safe environment without the need for water and enabling the use of eyeglasses if necessary.

Yet another object of this invention is to provide a shaving system and gel creams in which the gel cream is applied prior to shaving to the dry skin surface by placing a small amount on the fingertips and rubbing it briskly onto the skin area to be shaved in the form of a thin film. After shaving, the light residue is rubbed thoroughly into the just shaven skin areas and any adjacent or other nonshaven areas to provide skin enhancement by softening fine lines thereby providing a smoother, healthier and younger looking skin tone.

Another significant use area of the shaving system and gel creams is in hospitals, nursing homes and similar institutions which facilitates blade shaving in bed by avoiding the use of pans of water and consequent wet bed linens, towels and the like while at the same time providing much needed skin moisturization and enhancement in an environment known to cause dry, irritating skin conditions. Also, the invention is especially useful to members of military units, campers, hikers, boaters and others engaged in various recreational and professional endeavors in which a supply of potable water is not available. Further, the invention is equally beneficial when used with a disposable razor or a razor which uses a replaceable cartridge.

These together with other objects and advantages which will become subsequently apparent reside in the details of construction and operation as more fully hereinafter described and claimed, wherein like numerals refer to like parts throughout.

DESCRIPTION OF THE PREFERRED EMBODIMENTS

The shaving system and gel creams of the present invention are especially beneficial when used with resilient razors disclosed in co-pending applications Ser. No. 08/149,273 filed Nov. 9, 1993 U.S. Pat. No. 5,560,106 entitled RESILIENT FLOATING HEAD RAZOR and Ser. No. 08/226,349 filed Apr. 12, 1994 now abandoned entitled RAZOR CONSTRUCTION. The disclosure in the above co-pending applications is incorporated herein by reference thereto. The gel creams developed for use in the waterless shaving system are identified as "CL35" and include ten formulas or examples as follows:

Formula #1

Formula for Cl-35 Gelcream with Vitamin A,E, & C, Aloe Vera, NO-Fragrance

| MATERIAL | AMOUNTS - % W/W |
|---|---|
| Water | 50–70% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| Glyceryl Stearate | .2–8% |
| Glycol Stearate | .15–8% |
| Cetyl Alcohol | 1–5% |

-continued

| MATERIAL | AMOUNTS - % W/W |
|---|---|
| Acetylated lanolin | 1–8% |
| Sorbitan Oleate | .2–4% |
| Candelilla Wax | .5–3% |
| Laureth-23 | .5–5% |
| Magnesium Aluminum Silicate | .1–10% |
| Triethanolamine | .1–5% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100% |

Formula #2

Formula for Cl-35 Gelcream with Vitamin A,E, & C, Aloe Vera, Fragrance

| MATERIAL | AMOUNTS - % W/W |
|---|---|
| Water | 50–70% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth-23 | .5–5% |
| Magnesium Aluminum Silicate | .1–10% |
| Triethanolamine | .1–5% |
| Fragrance | .05–1% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100% |

Formula #3

Formula for Cl-35 Gelcream with Vitamin A,E, & C and SPF 15, and Aloe Vera, NO-Fragrance

| MATERIAL | AMOUNTS - % W/W |
|---|---|
| Water | 40–60% |
| Mineral Oil | 5–10% |
| Isopropyl Palmitate | 1–15% |

-continued

| MATERIAL | AMOUNTS - % W/W |
|---|---|
| Petrolatum | 1–10% |
| Glycerin | .6–10% |
| Stearic Acid | .5–10% |
| Ceresin | .2–4% |
| Octyl Methoxycinnamate | 2.5–8% |
| Octyl Salicylate | 3.5–10% |
| Benzophone 3 | 5.0–8.0% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth-23 | .5–5% |
| Magnesium Aluminum Silicate | .1–10% |
| Triethanolamine | .1–5% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100% |

Formula #4

Formula for Cl-35 Gelcream with Vitamin A,E, & C and SPF 15, Fragrance and Aloe Vera

| MATERIAL | AMOUNTS - % W/W |
|---|---|
| Water | 40–60% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| Octyl Methoxycinnamate | 2.5–8% |
| Octyl Salicylate | 3.5–10% |
| Benzophone 3 | 5.0–8.0% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth-23 | .5–5% |
| Magnesium Aluminum Silicate | .1–10% |
| Triethanolamine | .1–5% |
| Fragrance | .05–1% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Aloe Vera Gel | 1–5% |
| Vitamin A Acetate | .05–.5% |
| Vitamin E Acetate | .1–5% |
| Vitamin C (ascorbic acid) | .05–3% |
| TOTAL | 100% |

Formula #5

Formula for Cl-35 Gelcream with Vitamin A,E, & C and SPF 8, Aloe Vera Sunless Tanning, NO Fragrance

| MATERIAL | AMOUNTS - % W/W |
|---|---|
| Water | 50–70% |
| Mineral Oil | 5–10% |
| Isopropyl Palmitate | 1–15% |
| Petrolatum | 1–10% |
| Glycerin | .5–10% |
| DiHydroxy Acetone | .1–5% |
| Stearic Acid | .5–10% |
| Ceresin | .2–4% |
| Octyl Methoxycinnamate | 2.5–8% |
| Octyl Salicylate | 2–5% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth-23 | .5–5% |
| Magnesium Aluminum Silicate | .1–10% |
| Triethanolamine | .1–5% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100% |

Formula #6

Formula for Cl-35 Gelcream with Vitamin A,E, & C and SPF 8, Aloe Vera Sunless Tanning, Fragrance

| MATERIAL | AMOUNTS - % W/W |
|---|---|
| Water | 50–70% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| Octyl Methoxycinnamate | 2.5–8% |
| Octyl Salicylate | 2–5% |
| Glyceryl Stearate | .2–8% |
| DiHydroxy Acetone | .1–5% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth-23 | .5–5% |
| Magnesium Aluminum Silicate | .1–10% |
| Triethanolamine | .1–5% |
| Fragrance | .05–1% |
| Methylparaben | .005–.25% |
| Propylparaben | .005–.25% |
| Carbomer 934 | .01–3% |
| Dimethicone | .01–3% |
| D&C Yellow 10 | .0001–.1% |

-continued

| MATERIAL | AMOUNTS - % W/W |
|---|---|
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100% |

Formula #7

Formula for Cl-35 Gelcream with Vitamin A,E, & C, Aloe Vera and SPF 4, Lite Sunless Tanning, Light Fragrance

| MATERIAL | AMOUNTS - % W/W |
|---|---|
| Water | 50–70% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| DiHydroxy Acetone | .1–5% |
| Octyl Methoxycinnamate | 2.5–8% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth-23 | .5–5% |
| Magnesium Aluminum Silicate | .1–10% |
| Triethanolamine | .1–5% |
| Fragrance | .05–1% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100% |

Formula #8

Formula for Cl-35 Gelcream, Lite Tanning SPF 15 with Vitamins A,E, C and Fragrance, Aloe Vera

| MATERIAL | AMOUNTS - % W/W |
|---|---|
| Water | 40–65% |
| Mineral Oil | 5–10% |
| Isopropyl Palmitate | 1–15% |
| Petrolatum | 1–10% |
| Glycerin | .5–10% |
| Stearic Acid | .5–10% |
| DiHydroxy Acetone | .1–5% |
| Ceresin | .2–4% |
| Octyl Methoxycinnamate | 2.5–10% |
| Octyl Salicylate | 1.0–4% |
| Benzophone 3 | 3–8% |

-continued

| MATERIAL | AMOUNTS - % W/W |
|---|---|
| Titanium Dioxide | 1–5% |
| Glyceryl Stearate | .2–8% |
| Glycol Stearate | 15–8% |
| Cetyl Alcohol | 1–5% |
| Acetylated lanolin | 1–8% |
| Sorbitan Oleate | .2–4% |
| Candelilla Wax | 5–3% |
| Laureth-23 | .5–5% |
| Magnesium Aluminum Silicate | .1–10% |
| Triethanolamine | .1–5% |
| Fragrance | .05–.5% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Aloe Vera Gel | 1–5% |
| Vitamin E Acetate | .1–5% |
| Vitamin C | .1–3% |
| Vitamin A | .1–5% |
| TOTAL | 100% |

Formula #9

Formula for Cl-35 Gelcream Light Sunless Tanning with Vitamines A,E,C Aloe Vera Gel and Fragrance

| MATERIAL | AMOUNTS - % W/W |
|---|---|
| Water | 50–70% |
| Mineral Oil | 5–10% |
| Isopropyl Palmitate | 1–12% |
| Petrolatum | 1–12% |
| Glycerin | .5–10% |
| Stearic Acid | .5–10% |
| Ceresin | .2–4% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Fragrance | .05–1% |
| Methylparaben | .005–.25% |
| Propylparaben | .005–.25% |
| Carbomer 934 | .01–3% |
| Dimethicone | .01–5% |
| D&C Yellow 10 | .0001–.1% |
| Disodium EDTA | .002–.5% |
| Propylene Glycol | .05–5% |
| DiHyroxyactetone | 1–8% |
| Aloe Vera Gel | 1–5% |
| Vitamine A Acetate | .1–.3% |
| Vitamine E Acetate | 2–5% |
| Vitamine C | .1–2% |
| TOTAL | 100% |

Formula #10

Formula for Cl-35 Gelcream Light Sunless Tanning with Vitamines A,E,C Aloe Vera Gel and Fragrance, Natural Sunscreen SPF-2

| MATERIAL | AMOUNTS - % W/W |
|---|---|
| Water | 45–70% |
| Mineral Oil | 5–10% |
| Isopropyl Palmitate | 1–15% |
| Petrolatum | 1–15% |
| Glycerin | .5–10% |
| Stearic Acid | .5–10% |
| Ceresin | .2–4% |
| Glyceryl Stearate | .2–8% |
| Glycol Stearate | .15–8% |
| Titanium Dioxide | 2–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Fragrance | .05–1% |
| Methylparaben | .005–.25% |
| Propylparaben | .005–.25% |
| Carbomer 934 | .01–3% |
| Dimethicone | .01–8% |
| D&C Yellow 10 | .0001–.1% |
| Disodium EDTA | .002–.5% |
| Propylene Glycol | .05–5% |
| DiHyroxyactetone | 1–8% |
| Aloe Vera Gel | 1–5% |
| Vitamine A Acetate | .1–.3% |
| Vitamine E Acetate | 2–5% |
| Vitamine C | .1–2% |
| TOTAL | 100% |

In using the gel creams from a 3.5 fluid ounce (105 cc) tube the following total indicates minimum quantities for successful shaving and skin area application.

RESILIENT CL-35 CONSUMPTION USE
EVALUATION DATA ILLUSTRATING MINIMUM APPLICATION

MEN

| | |
|---|---|
| Face - shaven area only | .50 cc |
| Facial - including forehead, eyelids and sockets, nose, and unshaven neck area (additional) | .25 cc |
| Both arms, elbows, and hands | 3.00 cc |
| Jock itch prevention (inner thighs) - both legs | .50 cc |
| Feet, from ankles down | 1.50 cc |
| Both legs | 5.50 cc |
| Back (waist up) and chest | 2.50 cc |
| Average per shave (only) | .50 cc |
| Average (30-day) monthly consumption, daily, shaving only | 15.00 cc |
| Facial including shaven area | .75 cc |
| Average monthly shaving/facial consumption | 22.50 cc |
| Conclusion | |
| Average daily consumption for men's shaving/facial and other body areas | 4.00–5.00 cc |
| Average monthly consumption for men's shaving/facial and other body areas (approx. 1/3 tube of CL-35 per week) | 130.00–150.00 cc |

WOMEN

| | |
|---|---|
| Both legs, shaven area (knees down) | 3.00 cc |
| Bikini line, shaven area | .50 cc |

-continued

RESILIENT CL-35 CONSUMPTION USE
EVALUATION DATA ILLUSTRATING MINIMUM APPLICATION

| | |
|---|---|
| Both underarms, shaven area | .50 cc |
| Both arms, elbows, and hands | 2.00 cc |
| Both legs, unshaven area (knees up) | 2.00 cc |
| Entire back and shoulders | 1.25 cc |
| Both feet | 1.00 cc |
| Average use per shave | 4.00 cc |
| Average (30-day) monthly consumption, daily, shaving only (shaving every third day) | 40.00 cc |
| Average (30-day) monthly consumption, daily, shaving only (shaving daily) | 120.00 cc |
| Conclusion | |
| Average daily consumption for women's shaving every third day and treating other body areas daily | 7.00–8.00 cc |
| Average monthly consumption for women's shaving every third day and treating other body areas daily (approx. 1/2 tube of CL-35 per week) | 210.00–240.00 cc |

NOTE:
1 fl. oz. = 30 cc = 1.0 oz. net wt.
A 3.5-fl. oz. tube of CL-35 contains 105 cc (net wt. 3.5 oz.)

In utilizing the gel creams, the small quantity of gel cream, as indicated in the prior table is applied briskly to unwetted skin by the use of the fingertips and/or adjacent surfaces of the fingers and hand to leave a very light film. A resilient razor and blade with large exhaust ports is then used by shaving in a conventional manner. After shaving, the light residue remaining on the skin area is rubbed briskly into the skin area with the gel cream providing an effective moisturizer. The gel cream used with the resilient razor produces the closest, quickest and most comfortable shave and eliminates existing problems and discomfort associated with shaving. Some of the formulas contain sun protection factor (SPF) ranging from 2 to 15 to afford protection from skin damage due to the rays of the sun. Various fragrance materials can be added to the gel creams thereby providing an effective skin enhancement, sunless tanning and desirable fragrance. Various models or shelf keeping units (SKU) will have different fragrance materials, sun ray protectants or blockers, "no sun" tanning material or other skin enhancement materials. All formulas include vitamins A, C and E, aloe, moisturizers and in formula 10, the SPF2 is a natural sunscreen that is not derived from sunscreen chemicals. Some of the formulas include sunless tanning which are for everyday use and produce a very light tan within 4 to 5 days and will not get any darker. These formulas, when used everyday, provide a healthy tan glow, as opposed to other sunless formulas that produce a dark beach or tanning parlor look and must be regulated so that the skin does not get too dark.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. A method of shaving without requiring the presence of a source of water to wash, wet or soak the skin surface area to be shaved consisting of the steps of applying a shaving product in the form of a thin transparent film of lubricant gel cream to a dry, unwetted skin surface area to be shaved without prior application of water to the skin surface area, said transparent film of gel cream leaving the hair shaft in unwetted erect substantially rigid condition and in generally perpendicular relation to the skin surface area to be shaved and enable observation of skin blemishes, pimples, and moles by a person when moving a razor and blade assembly alone the skin surface area to eliminate cutting, nicking and scraping of the skin blemishes, pimples, and moles, moving a razor and blade assembly along the skin area in a manner to cut the erect hair with a straight transverse cut in substantially perpendicular relation to the hair shaft in close proximity to the skin surface area and entrain cut hair in the gel cream, removing the razor and blade assembly and gel cream from contact with the skin surface area after cutting the hair therefrom and manually rubbing residual shaving product into the shaved skin surface area and other skin areas without applying water to the shaved skin surface area for washing off the shaving product with the residual shaving product providing skin enhancement and protection.

2. The method as defined in claim 1 wherein the step of applying a shaving product to a skin surface area includes the application of skin enhancement materials incorporated into the shaving product including material to moisturize and lubricate the skin surface area to enable movement of the razor and blade assembly without skin irritation, razor burn and scraping or cutting the skin surface area.

3. The method as defined in claim 2 wherein said steps of applying a shaving product to the dry, unwetted skin area and rubbing residual shaving product into the skin area includes the step utilizing the palm surface ot the fingertip areas to briskly apply the shaving product and briskly rub in the residual shaving product to provide skin enhancement and protection thereby enabling the complete shaving operation to be conducted in areas without a supply of water.

4. The method as defined in claim 1 wherein said shaving product includes ingredients as follows:

| MATERIAL | AMOUNTS - % W/W |
| --- | --- |
| Water | 50–70% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100%. |

5. The method as defined in claim 1 wherein said shaving product includes ingredients as follows:

| MATERIAL | AMOUNTS - % W/W |
| --- | --- |
| Water | 50–70% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Fragrance | .05–1% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100%. |

6. The method as defined in claim 1 wherein said shaving product includes ingredients as follows:

| MATERIAL | AMOUNTS - % W/W |
| --- | --- |
| Water | 40–60% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| Octyl Methoxycinnamate | 2.5–8% |
| Octyl Salicylate | 3.5–10% |
| Benzophone 3 | 5.0–8.0% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100%. |

7. The method as defined in claim 1 wherein said shaving product includes ingredients as follows:

| MATERIAL | AMOUNTS - % W/W |
|---|---|
| Water | 40–60% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| Octyl Methoxycinnamate | 2.5–8% |
| Octyl Salicylate | 3.5–10% |
| Benzophone 3 | 5.0–8.0% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Fragrance | .05–1% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Aloe Vera Gel | 1–5% |
| Vitamin A Acetate | .05–.5% |
| Vitamin E Acetate | .1–5% |
| Vitamin C (ascorbic acid) | .05–3% |
| TOTAL | 100%. |

8. The method as defined in claim 1 wherein said shaving product includes ingredients as follows:

| MATERIAL | AMOUNTS - % W/W |
|---|---|
| Water | 50–70% |
| Mineral Oil | 5–10% |
| Isopropyl Palmitate | 1–15% |
| Petrolatum | 1–10% |
| Glycerin | .5–10% |
| DiHyroxy Acetone | .1–5% |
| Stearic Acid | .5–10% |
| Ceresin | .2–4% |
| Octyl Methoxycinnamate | 2.5–8% |
| Octyl Salicylate | 2–5% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100%. |

9. The method as defined in claim 1 wherein said shaving product includes ingredients as follows:

| MATERIAL | AMOUNTS - % W/W |
|---|---|
| Water | 50–70% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| Octyl Methoxycinnamate | 2.5–8% |
| Octyl Salicylate | 2–5% |
| Glyceryl Stearate | .2–8% |
| DiHydroxy Acetone | .1–5% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Fragrance | .05–1% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |
| Vitamin E Acetate | .1–5% |
| Vitamin C (ascorbic acid) | .05–3% |
| TOTAL | 100%. |

10. The method as defined in claim 1 wherein said shaving product includes ingredients as follows:

| MATERIAL | AMOUNTS - % W/W |
|---|---|
| Water | 50–70% |
| Mineral Oil | 5–10% |
| Isopropyl Palmitate | 1–15% |
| Petrolatum | 1–10% |
| Glycerin | .5–10% |
| Stearic Acid | .5–10% |
| Ceresin | .2–4% |
| DiHydroxy Acetone | .1–4% |
| Octyl Methoxycinnamate | 2.5–8% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Fragrance | .05–1% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Vitamin A Acetate | .05–.5% |
| Aloe Vera Gel | 1–5% |

-continued

| MATERIAL | AMOUNTS - % W/W |
|---|---|
| Vitamin E Acetate | .1–5% |
| Vitamin C (ascorbic acid) | .05–3% |
| TOTAL | 100%. |

11. The method as defined in claim 1 wherein said shaving product includes ingredients as follows:

| MATERIAL | AMOUNTS - % W/W |
|---|---|
| Water | 40–65% |
| Mineral Oil | 5–10% |
| Isopropyl Palmitate | 1–15% |
| Petrolatum | 1–10% |
| Glycerin | .5–10% |
| Stearic Acid | .5–10% |
| DiHydroxy Acetone | .1–5% |
| Ceresin | .2–4% |
| Octyl Methoxycinnamate | 2.5–10% |
| Octyl Salicylate | 1.0–4% |
| Benzophone 3 | 3–8% |
| Titanium Dioxide | 1–5% |
| Glyceryl Stearate | .2–8% |
| Glycol Stearate | 15–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Fragrance | .05–.5% |
| Methylparaben | .005–.25% |
| Propylparaben | .005–.25% |
| Carbomer 934 | .01–3% |
| Dimethicone | .01–3% |
| D&C Yellow 10 | .0001–.1% |
| Disodium EDTA | .002–.5% |
| Propylene Glycol | .05–5% |
| Aloe Vera Gel | 1–5% |
| Vitamin E Acetate | .1–5% |
| Vitamin C | .1–3% |
| Vitamin A | .1–5% |
| TOTAL | 100%. |

12. The method as defined in claim 1 wherein said shaving product includes ingredients as follows:

| MATERIAL | AMOUNTS - % W/W |
|---|---|
| Water | 50–70% |
| Mineral Oil | 5–10% |
| Isopropyl Palmitate | 1–12% |
| Petrolatum | 1–12% |
| Glycerin | .5–10% |
| Stearic Acid | .5–10% |
| Ceresin | .2–4% |
| Glyceryl Stearate | .2–8% |
| Glycol Stearate | .15–8% |
| Cetyl Alcohol | 1–5% |
| Acetylated lanolin | 1–8% |
| Sorbitan Oleate | .2–4% |

-continued

| MATERIAL | AMOUNTS - % W/W |
|---|---|
| Candelilla Wax | .5–3% |
| Laureth - 23 | .5–5% |
| Magnesium Aluminum Silicate | .1–10% |
| Triethanolamine | .1–5% |
| Fragrance | .05–.5% |
| Methylparaben | .005–.25% |
| Propylparaben | .005–.25% |
| Carbomer 934 | .01–3% |
| Dimethicone | .01–5% |
| D&C Yellow 10 | .0001–.1% |
| Disodium EDTA | .002–.5% |
| Propylene Glycol | .05–5% |
| DiHyroxyacetone | 1–8% |
| Aloe Vera Gel | 1–5% |
| Vitamine A Acetate | .1–.3% |
| Vitamine E Acetate | 2–5% |
| Vitamin C | .1–2% |
| TOTAL | 100%. |

13. The method as defined in claim 1 wherein said shaving product includes ingredients as follows:

| MATERIAL | AMOUNTS - % W/W |
|---|---|
| Water | 45–70% |
| Mineral Oil | 5–10% |
| Isopropyl Palmitate | 1–15% |
| Petrolatum | 1–15% |
| Glycerin | .5–10% |
| Stearic Acid | .5–10% |
| Ceresin | .2–4% |
| Glyceryl Stearate | .2–8% |
| Glycol Stearate | .15–8% |
| Titanium Dioxide | 2–8% |
| Cetyl Alcohol | 1–5% |
| Acetylated lanolin | 1–8% |
| Sorbitan Oleate | .2–4% |
| Candelilla Wax | .5–3% |
| Laureth - 23 | .5–5% |
| Magnesium Aluminum Silicate | .1–10% |
| Triethanolamine | .1–5% |
| Fragrance | .05–.5% |
| Methylparaben | .005–.25% |
| Propylparaben | .005–.25% |
| Carbomer 934 | .01–3% |
| Dimethicone | .01–8% |
| D&C Yellow 10 | .0001–.1% |
| Disodium EDTA | .002–.5% |
| Propylene Glycol | .05–5% |
| DiHyroxyacetone | 1–8% |
| Aloe Vera Gel | 1–5% |
| Vitamine A Acetate | .1–.3% |
| Vitamine E Acetate | 2–5% |
| Vitamin C | .1–2% |
| TOTAL | 100%. |

14. The method as defined in claim 1 wherein approximately 0.50 cc of said shaving product is applied to the skin surface area to be shaved when used by men for facial shaving.

\* \* \* \* \*